United States Patent [19]

Talal et al.

[11] Patent Number: 5,320,940

[45] Date of Patent: Jun. 14, 1994

[54] METHODS AND COMPOSITIONS FOR IDENTIFYING AND CHARACTERIZING INDIVIDUALS HAVING AUTOIMMUNE RHEUMATIC DISEASES

[75] Inventors: Norman Talal, San Antonio, Tex.; Robert F. Garry, New Orleans, La.

[73] Assignee: Board of Regents, The University of Texas System, Austin, Tex.

[21] Appl. No.: 981,950

[22] Filed: Nov. 25, 1992

Related U.S. Application Data

[63] Continuation of Ser. No. 354,273, May 19, 1989, abandoned.

[51] Int. Cl.$^5$ .......................... C12Q 1/70; C12Q 1/00; G01N 33/566; G01N 33/564
[52] U.S. Cl. .......................................... 435/5; 435/7.1; 436/501; 436/506; 436/507; 930/221
[58] Field of Search ..................... 435/5, 7.1; 436/506, 436/507; 930/221

[56] References Cited

U.S. PATENT DOCUMENTS 4,877,725  10/1989  Neurath et al. ........................ 435/5

OTHER PUBLICATIONS

Talal, et al., *J. Clin. Invest.*, vol. 85, Jun. 1990, 1866–1871.
Talal, et al., *Arthritis and Rheumatism*, vol. 33, No. 6, Jun. 1990, pp. 774–781.
Narayan et al., Ann. Neurol. (USA), 1988, 23/supp. pp. S95-S100. Abstract only.
Dalakas et al., *JAMA* Nov. 7, 1986, 256 (17) pp. 2381–2383; abstract only.
McDougal. *Arthritis Rheum.* 28(10), pp. 1170–1174, 1985. (Full Article).
Takei, M. et al., Clin. Exp. Immunol., 70:546–554 (1987).
Talal (1983), *Immunology Today*, 4:180–183.
Talal (1985), *Rheumatology*-85, pp. 365–369.
Talal (1986), *Scand. J. Rheumatology*, 61:76–82.
Talal (Jan., 1989), "Etiologic Mechanisms" in *The Many Faces of Sjogren's Syndrome*, A Conference for Physicians, Dentists, and Other Health Professionals, The National Institute of Arthritis and Musculoskeletal and Skin Diseases.
"Detection of Serum Antibodies to Retroviral Proteins in Patients With Primary Sjogen's Syndrome (Autoimmune Exocrinopathy)"; *Arthritis and Rheumatism*, vol. 22, No. 6, (Jun. 1990).
"A Conserved Idiotype and Antibodies to Retroviral Proteins in Systemic Lupus Erythematosus"; *Journal of Clinical Investigation*, vol. 85, pp. 1866–1871, Jun. 1990.
"Detection of a Human Intracisternal A-Type Retroviral Particle Antigenically Related to HIV."; *Science*, vol. 259, pp. 1127–1129.
"Scientists Reveal Discovery of New AIDS-Like Virus"; *Houston Chronicle*, Friday, Nov. 23, 1990, Nation.
Plapp, F. V., et al., The Lancet, Jun. 28, 1986, 1465–1466.
Alric, M., et al., Anal. Biochemistry, 155:328–334 (1986).
Araujo, F. G., Am. J. Trop. Med. Hyg., 34(2):242–245 (1985).
Meusing, M. A., et al., Nature, 313: 450–458 (Feb. 7, 1985).
Ratner, L., et al., Nature, 313: 277–284 (Jan. 24, 1985).

*Primary Examiner*—Margaret Parr
*Assistant Examiner*—Bradley L. Sisson
*Attorney, Agent, or Firm*—Arnold, White & Durkee

[57] ABSTRACT

Diagnostic assays wherein sera from a patient suspected of having an ill defined autoimmune rheumatic disease is reacted with antigens specific to the human immunodeficiency virus (HIV) core proteins (gag protein products p24 or p17) and envelope proteins env (protein products gp41 and gp160). Immunoreactivity is determined by the formation of an antibody-antigen complex as observed in a Western immunoblot assay. The degree of cross reactivity to the 4 individual proteins is determined, and with this information, a specific and more accurate diagnosis of the disease is made. Once a more accurate diagnosis is determined, the clinician may then proceed with prescribing a therapeutic regimen better suited for the specific patient.

10 Claims, 6 Drawing Sheets

METHODS AND COMPOSITIONS FOR IDENTIFYING AND CHARACTERIZING INDIVIDUALS HAVING AUTOIMMUNE RHEUMATIC DISEASES

This application is a continuation of application Ser. No. 07/354,273, filed May 19, 1989, now abandoned.

BACKGROUND OF THE INVENTION

The government may own certain rights in the present invention pursuant to grants from the General Medical Research Service of the Veterans Administration, as well as USPHS grant number AM30487.

FIELD OF INVENTION

The present invention is directed to methods and compositions useful for identifying and characterizing patients having autoimmune rheumatic diseases. In particular aspects, this invention relates to diagnostic assays including immunological, primer or probe-based, capable of identifying a subset of autoimmune rheumatic disease patients exhibiting one or more class-specific retroviral antigens, antibodies to such antigens, or nucleic acid sequences coding therefor.

DESCRIPTION OF THE RELATED ART

Autoimmune rheumatic diseases afflict a significant proportion of the American population. Rheumatic diseases resemble rheumatism by one or more features, rheumatism being defined as an indefinite term applied to various conditions with pain or other symptoms which are of articular origin (relating to a joint) or related to other elements of the musculoskeletal system. Five of the more common autoimmune rheumatic diseases are: rheumatoid arthritis (RA), scleroderma (S), Sjogren's syndrome (SS), systemic lupus erythematosus (SLE) and polymyositis (P).

Millions of Americans are diagnosed each year with rheumatoid arthritis (inflammatory joint pain) and approximately one-quarter of these RA patients are diagnosed as also having secondary Sjogren's syndrome. Rheumatoid arthritis is characterized by severe joint pain due to inflammation and swelling. The severity of the pain often achieves levels which can potentially incapacitate the patient thus preventing the patient from working or from performing basic tasks (i.e. buttoning a button, opening a jar of jelly, etc.). Primary Sjogren's syndrome is characterized by different symptoms which include dryness of mucous membranes (eyes and mouth) and bilateral parotid enlargement. SS is considered a benign autoimmune disease characterized by lymphoid infiltration of salivary and lacrimal glands often accompanied by autoantibodies, particularly anti-Ro and anti-La. Some SS patients develop a more generalized lymphoproliferative disease which can be associated with monoclonal immunoglobulins. Autoimmunity is defined as the condition in which one's own tissues are subject to deleterious effects of the immunological system.

Three more autoimmune rheumatic diseases, namely, systemic lupus erythematosus, scleroderma and polymyositis present serious health problems, afflicting hundreds or thousands of Americans each year. SLE is characterized by an inflammation of connective tissues with variable features frequently including fever, weakness, joint pains or arthritis resembling rheumatoid arthritis, diffuse erythematosus skin lesions on the face, neck and upper extremities, degeneration of the basal layer and epidermal atrophy and other evidence of an autoimmune phenomenon. Similarly, scleroderma is characterized by thickening of the skin caused by swelling of fibrous tissue, with eventual atrophy of the epidermis. Polymyositis is characterized by severe inflammation of a number of voluntary muscles simultaneously.

From the characteristics presented above for the common autoimmune rheumatic diseases, it should be apparent that common, as well as, overlapping and shared symptoms exist for each of the diseases. For example, the natural history of SS also includes a different clinical presentation, one which is more overtly autoimmune and, at times, indistinguishable from SLE (1). In point of fact, SS and SLE can both be characterized by the presence of anti-Ro and anti-La autoantibodies. It is therefore not surprising that these two diseases share immunogenetic properties and that a true SS/SLE overlap syndrome has been recognized and documented (1). SS/SLE overlap syndrome is diagnosed when the patient presents clinical characteristics and symptoms for both diseases (SS and SLE).

Due to abnormal cellular immune functions common to both SS and acquired immune deficiency syndrome (AIDS), the present inventor has previously hypothesized a possible retroviral etiology for SS, and has reported a hypothesis that immunologic similarities exist between SS and AIDS (2). Moreover, Dauphinee et al. reported an increase in CD5 receptor-positive cells in both SS and AIDS (3) as well as RA (4,5). CD5 positive cells are present in neonatal life, and decrease in normal strains but persist in autoimmune strains (6). In the autoimmune strains, the CD5 positive cells become clonal and infiltrate parenchymal lymphoid organs, resembling an SS-like clinical presentation.

Similar indistinguishable characteristics often occur for many of the described autoimmune rheumatic diseases, more data is needed to accurately diagnose a patient as having, for example, SLE instead of SS. In particular, more scientific data is needed to specifically diagnose these patients. Without an accurate and specific diagnosis for the patient's disease, the clinician runs the risk of prescribing a therapy that is not only ineffective for that disease, but one which may ultimately hinder the efficacy of other treatments for that patient.

Thus, one can appreciate the importance, as well as the need, to rapidly and accurately diagnose a patient with a specific rheumatic disease. Since the patient's pain and discomfort is a major concern of the physician, the operative words from the above sentence are "rapid diagnosis". There is a need for a rapid assay that would further inform the clinician as to which autoimmune rheumatic disease the patient has. This rapid diagnosis would aid the clinician in properly prescribing a therapeutic regimen directed towards eliminating the patient's pain. Thus, a means of rapidly and accurately identifying those individuals with a specific autoimmune rheumatic disease would greatly facilitate the clinician's ability to define the etiology of that disease and to initiate the proper therapeutic regimen which effectively and quickly eliminates the patient's pain and discomfort.

SUMMARY OF THE INVENTION

The present invention addresses one or more disadvantages in the art by providing various methods for identifying or characterizing individuals having an autoimmune rheumatic disease, such as Sjogren's Syndrome (SS), rheumatic arthritis (RA), scleroderma (S), systemic lupus erythematosus (SLE) or polymyositis (P). The various methods of this invention are based in part on the inventor's discovery that a subset of individuals who are diagnosed to have or suspected of having, one of the foregoing or other autoimmune rheumatic diseases, exhibit antibodies against retroviral antigens and/or produce the antigens themselves, including the nucleic acid sequences encoding the antigens.

Known retroviruses, such as HIV-1 which causes AIDS and ARC (Aids-Related Complex), as well as other retroviruses known to be responsible for some human conditions, HTLV-I, HIV-2, etc., can be excluded as the basis for such antigen production and the observed anti-retroviral immune response. By way of theory, and not limitation, it is proposed that a novel retrovirus or class of retroviruses, termed Human Autoimmunity Virus, is interrelated or associated with, perhaps causally, a certain subclass of autoimmune rheumatic diseases. Additionally, the observation could be explained by "latent" viral genes that are somehow activated as a part of the occurrence of the disease or syndrome.

The invention has utility not only in diagnosing autoimmune rheumatic disease patients, but also in identifying that subset of individuals who are most likely to be amenable to therapeutic intervention, such as through the use of anti-retroviral agents such as AZT, specific immuno-blockers (e.g. CD5 in lieu of CD4 as in AIDS) and specific immunosuppressants (e.g. antiidiotype). The methods of the invention are thus directed to either identifying autoimmune rheumatic disease patients, e.g., as an initial screen of possible or suspected patients, or as a means of characterizing patients already known or believed to have one of the foregoing disease, as to whether the condition presented by that individual might have a retroviral-related component.

In certain embodiments, therefore, the invention concerns a method for identifying or characterizing individuals having an autoimmune rheumatic disease. In one embodiment, the method includes generally an initial step of obtaining a clinical sample that includes antibodies of an individual, e.g., one suspected of having an autoimmune rheumatic disease. Typically, and most conveniently, the clinical sample will be a blood sample from which serum is prepared. However, other samples such as saliva or cerebrospinal fluid may prove useful as a source of antibodies to be tested.

After obtaining the sample, proteins in the sample are characterized by determining the presence of antibodies to one or more group specific retroviral antigens, and absence of antibodies to one or more HIV-1-specific antigens. By testing the individual's antibodies for the absence of HIV-1 type-specific determinants, or those of other known retroviruses such as HTLV-I or HIV-2, a diagnosis of AIDS, ARC, T-lymphocytic leukemia, spastic paralysis or the like can be excluded. Where group-specific determinants, such as p24 or p17 gag proteins, are nonetheless identified in such individuals, such a characterization is indicative of an autoimmune rheumatic disease.

As used herein, the term "group-specific" sequence determinant or antigen, is intended to refer to a particular nucleic acid sequence, determinant, antigen, epitope, etc., that is common to or shared by most or all members of the particular group. The group of the present invention is retroviruses generally, and human retroviruses in particular. In contrast, "type-specific" is intended to refer to a nucleic acid sequence, antigen, determinant, epitope, etc., that is specific to the particular retroviral type, e.g., HIV-1, HIV-2, HTLV-I, etc.

In general, in the practice of the invention one will desire to target one or more selected group-specific retroviral antigen or antibody for immunological or other detection (e.g., detection of nucleic acid coding sequences) in such a way as to exclude the possibility of AIDS, ARC or related HIV-1 infections. This is preferably done by targeting both an HIV-1-specific as well as a group-specific retroviral antigen.

Typically, for the group-specific retroviral antigen one will desire to target a group-specific gag, env or pol retroviral antigen, with the most preferred being p24 or p17 gag proteins, particularly p24. To exclude the possibility of HIV-1 infection, one will generally further desire to target an HIV-1 specific antigen, preferably the gp41 or gp120 env proteins.

A finding of an antibody profile such as the foregoing will be indicative of an autoimmune rheumatic disease such as RA, S, SS, SLE, P, or the like. It is believed that between about one-third and one-half of SS patients will ultimately be found to exhibit an anti retroviral-positive, HIV-1-negative, profile. Many of the 4 million American SS patients go undiagnosed, in spite of their pain and suffering, because many doctors are unfamiliar with this disease. With this in mind, the treating physician may desire to have an HIV-1/Western blot assay run using the individual's serum antibodies, to identify a relative absence of anti-HIV-1 type-specific (e.g., gp41, gp120, gp160) antigens and presence of anti-retroviral group-specific (e.g., p24, p17) antigens. Additionally, this practice once established, will have the added advantage of helping diagnose another body of patients who have ill-defined rheumatic disease symptoms.

In other embodiments, the invention concerns a method for identifying such individuals through the detection of the respective retroviral antigens themselves, or nucleic acid sequences encoding them. For retroviral antigen or antigen-encoding nucleic acid detection, it will generally be the case that one will desire to screen those types of cells normally subject to retroviral infection, e.g., leukocytes or lymphocytes, in general, and B cells, T cells and macrophage populations and subsets of these populations more particularly. Thus, it will typically be most convenient to simply collect blood sample from the patient, and prepare leukocytes from the sample.

For antigen detection, one will generally desire to solubilize or otherwise extract proteins from the targeted cells. Generally, this is done by a technique called antigen capture assay. In order to characterize antigens, the proteins are then probed immunologically using specific anti-retroviral antibodies, such as antibodies having specificity for one of the foregoing retroviral antigens, e.g., p17, p24, gp41, gp120 and gp160.

As with antibody characterization, in order to predict a result, antigen characterization made by identification of the presence of one or more group specific retroviral antigens, and absence of one or more HIV-1 type-specific antigens, such a characterization being indicative of an autoimmune rheumatic disease. Antigens are then detected immunologically, by techniques known in the art (e.g., by ELISA, RIA, Western blot, etc.).

In still further embodiments, one may desire to target the nucleic acid coding sequences which form the basis of the genes which encode the respective antigens, determinants, etc., being detected, whether by a "virus", such as Human Autoimmune Virus, or some endogenous virus-like gene. As with antigen detection, both primers and probes are known in the art which can be applied to the detection of the foregoing group-specific and type-specific genes. Typically, for determining the presence or absence of retroviral or retroviral-like coding sequences, one will generally employ a leukocyte or lymphocyte DNA sample and, along with the particular primer or probes(s) (e.g., to p24, p17, gp41, gp120, etc.), perform a hybridization probe or polymerase chain primer extension assay.

In general, the detection of HIV, HTLV or retroviral antibodies, antigens and/or coding sequence is well known in the art, for example, as illustrated by the available techniques and kits for various antibodies, antigens or specific nucleic acid detection. Numerous techniques are known for hybridization analysis of HIV-1 antigen sequences by molecular hybridization (see, e.g., W08707912; and EP269520, incorporated herein), as well as for analysis of individual antigens or antibodies by immunological means (see, e.g., U.S. Pat. Nos. 4,520,113; 4,708,818; W08706620; and W08706005, incorporated herein).

HIV-1 proteins (strain HTLV-III$_B$, propagated in H9 cells) were resolved by NaDodSo$_4$-PAGE and then transferred to a nitrocellulose membrane. Strips of the nitrocellulose membrane were exposed to sera from SS patients, normal subjects, or individuals infected with HTLV-1 or HIV-2. Specifically bound IgG was visualized by standard enzyme-linked immunoblot techniques.
Lane a serum from a patient infected with HIV-1
Lanes b-u sera from SS patients
Lanes v-x sera from normal donors
Lane y serum from a patient infected with HTLV-1
Lane z serum from a patient infected with HIV-2

Figure 2A:
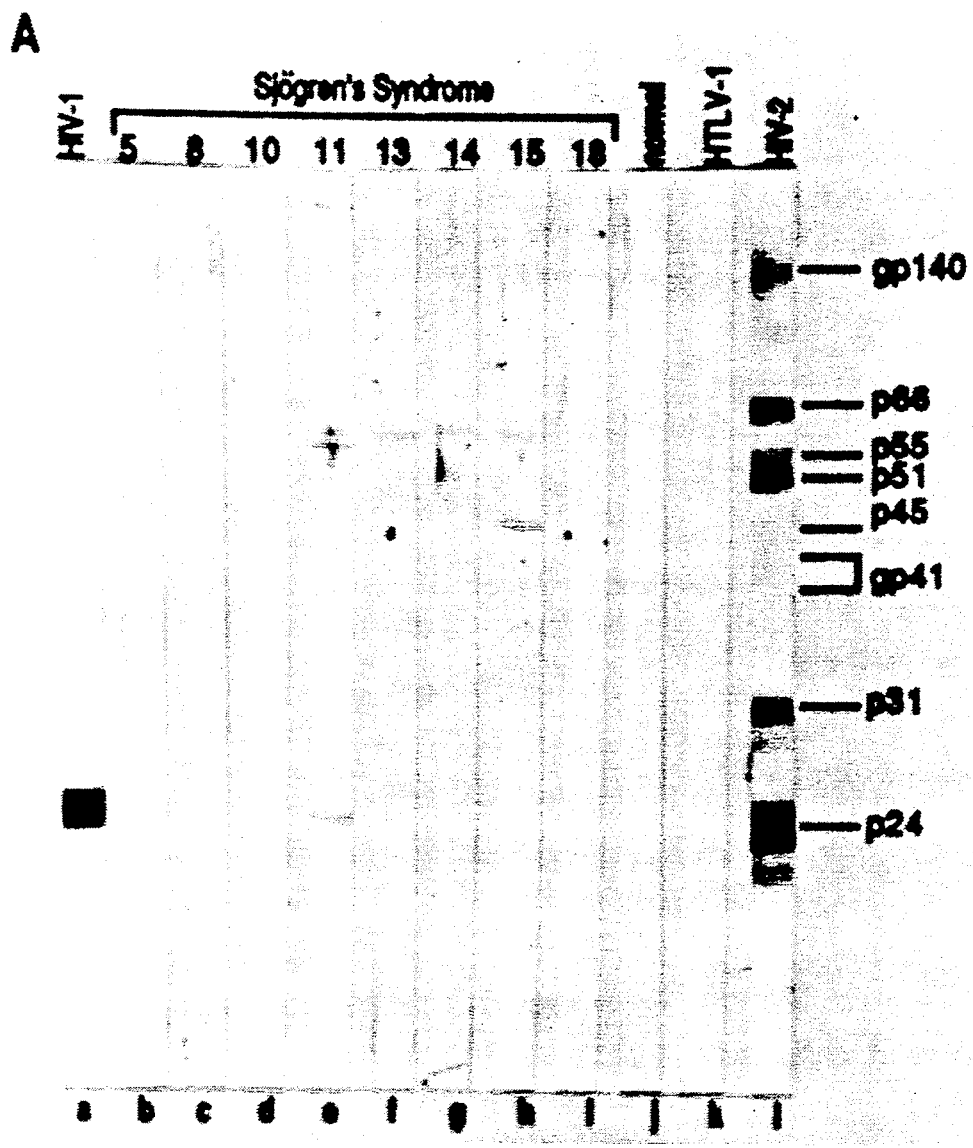
Figure 2B:
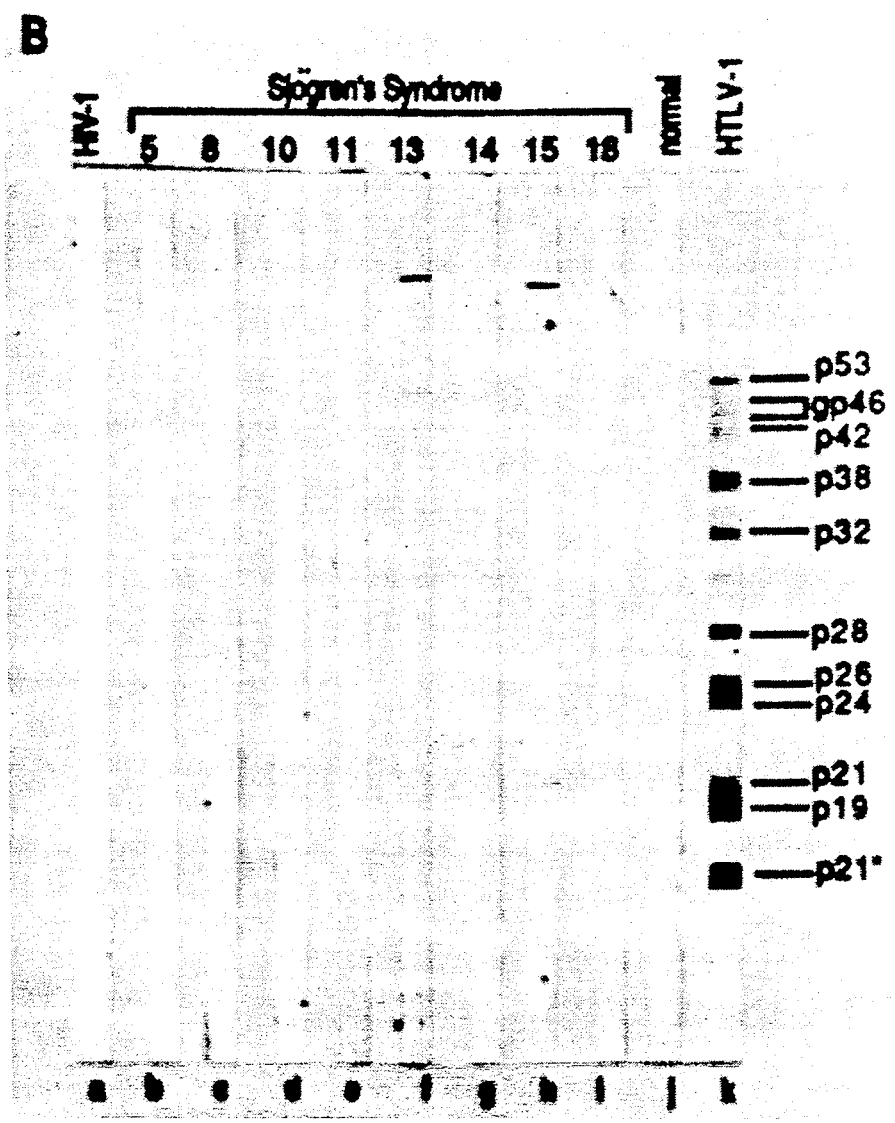

FIG. 2. Immunoblot Analysis of SS and Control Sera Reacting with HIV-2 and HTLV-1

Strips of the nitrocellulose membrane containing electrophoretically separated human retrovirus proteins were incubated with sera from AIDS or SS patients. IgG specifically bound to the proteins was visualized by standard enzyme-linked immunoblot techniques.
Panel: A HIV-2 (National Institutes of Health strain Z, propagated in HuT 78 cells) proteins.
Lane a serum from a patient infected with HIV-1
Lanes b-i sera from SS patients
Lane j serum from a normal donor
Lane k serum from a patient infected with HTLV-1
Lane l serum from a patient infected with HIV-2
Panel: B HTLV-1 (grown in HuT 102 strain B2) proteins containing in addition a recombinant envelope protein p21e (p21*) produced in E. coli.
Lane a serum from a patient infected with HIV-1
Lanes b-i sera from SS patients
Lanes j serum from a normal donor
Lanes k serum from a patient infected with HTLV-1

Figure 3A:
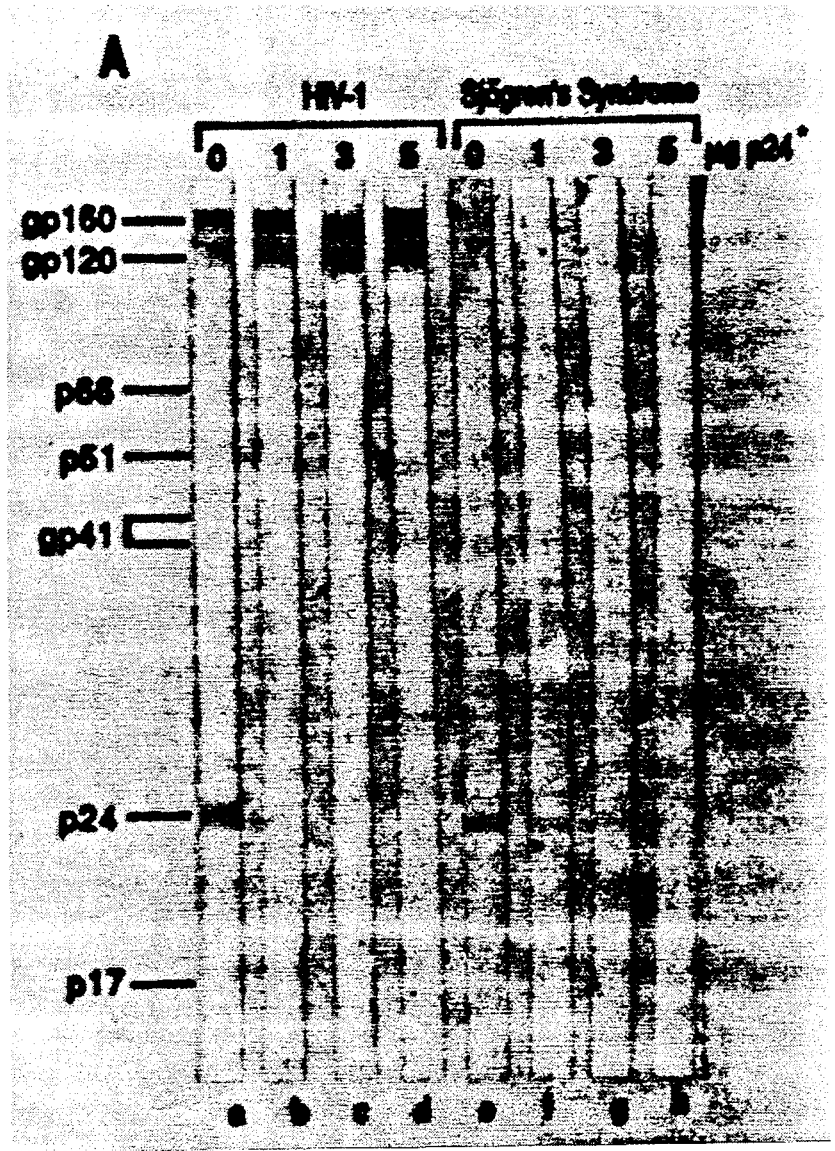

FIG. 3 Immunoblot Analysis of SS and Control Sera Reacting with Recombinant p24 (p24*)

Panel: A p24* (0-5 ug) was exposed for 4 hours in blotting buffer with either a HIV-1 serum or a SS patient serum. The sera were then exposed to strips of the nitrocellulose containing electrophoretically separated HIV-1 proteins. The ability of p24* to block the binding of antibodies in the sera to specific HIV-1 proteins was assessed by enzyme-linked immunoblot assay.
Lanes a-d serum from patient infected with HIV-1
Lanes e-h serum from SS patient
Panel: B The recombinant HIV-1 gag protein, p24*, was resolved by NaDodSo$_4$-PAGE, then transferred to a nitrocellulose membrane. Strips of the nitrocellulose membrane were exposed to sera from an AIDS patient, several SS patients, one normal subject, one individual infected with HTLV-1 and another infected with HIV-2. Specifically bound IgG was visualized by enzyme-linked immunoblot techniques.
Lane a serum from a patient infected with HIV-1
Lanes b-i sera from SS patients
Lane j serum from a normal donor
Lane k serum from a patient infected with HTLV-1
Lane l serum from a patient infected with HIV-2
p24* = A recombinant protein produced in the insect cell/baculovirus expression system (MicroGeneSys, Inc., West Haven, Conn.) derived from an HIV-1 gag gene fragment that includes all of p24 plus 12 amino acids of the C-terminus of p17 and 57 amino acids of the N-terminus of p15.

Figure 4:
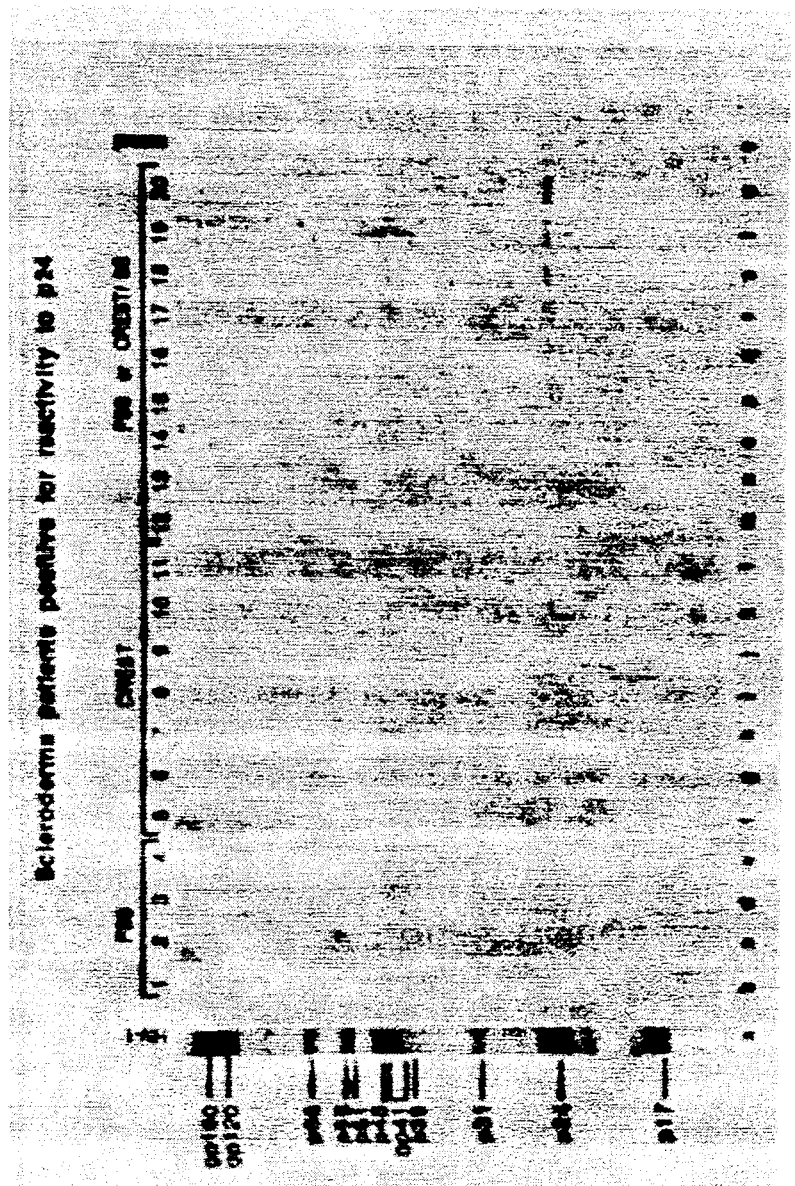

FIG. 4 Immunoblot Analysis of Scleroderma and Control Sera Reacting with HIV-1 proteins HIV-1 proteins (strain HTLV-III$_B$, propagated in H9 cells) were resolved by NaDodSo$_4$-PAGE and then transferred to a nitrocellulose membrane. Strips of the nitrocellulose membrane were exposed to sera from SS patients, normal subjects, or individuals infected with HIV-1, sera from PSS patients, CREST patients, PSS or CREST/SS overlap patients or a representative normal subject. Specifically bound IgG was visualized by standard enzyme-linked immunoblot techniques. PSS = Progressive Systemic Scleroderma, CREST = A clinical subset of scleroderma where C=calcinosis, R=Raynaud's Phenomemon, E=esophogial dysmotility, S=sclerodactyly, T=telangiectasias.
Lane a serum from a patient infected with HIV-1
Lanes b-e sera from PSS patients
Lanes f-l sera from CREST patients
Lane m-u sera from PSS or CREST/SS overlap patients
Lane v serum from a normal donor

DETAILED DESCRIPTION OF THE INVENTION

Retrovirus and Retroviral Diseases

Retroviruses are perhaps the ultimate parasites because they do not seriously damage the host cell once they stably integrate into the host cell's genome. The retroviral genome contains at least three open reading frames, 'gag', 'env' and 'pol', which encode respectively, the capsid proteins, the envelope proteins and the nonstructural proteins necessary for replication. These three translation products are virion proteins. The env protein is inserted into the lipid bilayer that surrounds the virus while the gag protein forms an inner shell of the virion. pol is often expressed as a hybrid product (a gag-pol protein), which contains the reverse transcriptase, and is also located inside the virus particle. The termination signal for gag is suppressed 10-15% of the time thus giving rise to the gag-pol hybrid. After the particles are formed, both the gag and the gag-pol products are extensively processed by proteolysis. These three structural protein products are known to be common to all retroviruses.

In 1980, the first plausible candidate for a human retrovirus, either oncogenic or non-oncogenic, was reported. This virus, human T-cell leukemia virus (HTLV), was distinct from the known animal tumor viruses, in that this viral infection was clearly associated with T-lymphocytic leukemia. How the HTLV virus causes the tumor is unknown.

The other known major human disease caused by a retrovirus is acquired immune deficiency syndrome (AIDS). The virus that is implicated in the cause of AIDS is different from the HTLV. The AIDS virus is known as HTLV-III or HIV-1. HTLV (described above) transforms T lymphocytes into continuously growing, immortal cells. In contrast, the AIDS-related retrovirus (HIV-1) does not immortalize T lymphocytes, but instead kills T lymphocytes (these are white blood cells which play a central role in the body's immune response). When these T lymphocytes are eliminated, one destroys a critical aspect of the body's immune defenses, thus, leaving the victim open to a wide range of infections. The virus infects both T lymphocytes and macrophages by entering these target cells through interacting with a molecule called CD4. Therefore, only cells bearing the CD4 receptor can be infected.

The specific viral binding takes place when an "envelope" glycoprotein of the HIV-1 called gp120 interacts with the CD4 receptor. This glycoprotein is distributed on the outside of the viral coat membrane. Another glycoprotein, gp41, becomes uncovered once the interaction between the gp120 glycoprotein and HIV occurs (precursor to gp120 and gp41 is gp160). One end of gp41 molecule is embedded into the macrophage or T cell membrane. This leads to the eventual fusion of the viral membrane and the cell membrane. Investigators are now identifying the specific portions of the CD4 and gp120 molecules that take part in the binding interaction. This information would make it possible to envision a two-pronged attack on HIV: denying access to the cellular CD4 receptor, both by covering up the viral gp120 protein and by blocking the receptor itself.

Molecularly, the HIV-1 virus particle is structurally similar to other retroviruses because of the common retroviral gag, pol and env protein products which encode for the structural components of the virus particle. However, there are at least 6 other genes which serve to regulate the expression of these virion genes. Several of these regulatory genes are divided into noncontiguous pieces. The gene segments are spliced together in the RNA transcript from which the protein is made. Since the DNA can be read in three reading frames, as many as three genes do coexist on one segment of DNA.

CD5 receptor positive cells are normally found on T lymphoctyes. However, CD5 positive B cells occur in SS, RA and AIDS. They are also involved with the etiology of chronic lymphocytic leukemia. Since the inventor's original hypothesis was presented in 1985, numerous reports have documented the development of a SS-like disorder in subjects infected with the human immunodeficiency virus (HIV-1; the AIDS virus). Moreover, T cells of SS patients demonstrate abnormalities of transmembrane signalling after exposure to PMA and /or ionomycin. These abnormalities are similar in nature to those that can be induced in normal T cells infected in vitro with HIV-1.

Of clinical interest, AIDS patients develop a variety of rheumatic, arthritic and dermatologic problems including an SS-like presentation characterized by salivary gland lymphoid infiltrates, glandular swelling, xerostomia, arthralgias, pulmonary lymphoid infiltrates and dry mouth (16-19). Autoantibodies (e.g. antinuclear arthritic factor and rheumatoid factor) have been detected in HIV-1 positive subjects (28), however, these patients lack both anti-Ro and anti-La autoantibodies. Infection with the HIV-1 should now be considered in any patient presenting an SS-like clinical picture. The absence of anti-Ro and anti-La autoantibodies favors a retrovirus infection over autoimmune exocrinopathy in the differential diagnosis.

Characterization of Sjogren's Syndrome

Primary Sjogren's Syndrome (SS) is considered a benign autoimmune disease characterized by lymphoid infiltration of salivary and lacrimal glands often accompanied by serum autoantibodies, particularly anti-Ro and anti-La. Some patients develop a more generalized lymphoproliferative disease (pseudolymphoma) which can be associated with monoclonal immunoglobulins. In 5-10% of patients, there may be a sudden transformation in the illness characterized by wasting, hypogammaglobulinemia, loss of autoantibodies, and the appearance of highly undifferentiated neoplastic cells in the salivary glands or in extrasalivary organs (9). These SS patients develop, even after two decades of benign disease, a potentially fatal malignant lymphoma, almost always belonging to the B cell lineage (14). Both SS and SLE are characterized by the presence of anti-Ro and anti-La autoantibodies. They also have close immunogenetic similarities. Moreover, a true SS/SLE overlap syndrome is recognized (15). Some primary SS patients closely resemble (and occasionally are difficult to distinguish from) systemic lupus erythematosus (SLE) (15).

The lymphocytes become more aggressive in approximately 70% of patients, infiltrating and compromising function in the lungs, kidneys, and muscles. Monoclonal immunoglobulins can be present in the serum (9,10) urine (11) or in cryoprecipitates (12). Local or generalized lymphadenopathy may develop (9). Lymph node excision or parenchymal organ biopsy may suggest lymphoid malignancy. DNA hybridization studies performed on these biopsy specimens demonstrate monoclonal immunoglobulin gene rearrangements (13); immunoperoxidase studies reveal monoclonal immunoglobulins (14). In some patients, it can be extremely difficult to determine whether the lymphoid infiltrates are benign or malignant. The term pseudolymphoma, now over two decades old (10), is still used to characterize this condition.

There are immunologic similarities between primary SS patients and AIDS patients. For example, there are increased numbers of CD5+ B cells in both diseases. Moreover, T cells of SS patients demonstrate abnormalities of transmembrane signalling after exposure to PMA and/or ionomycin similar to abnormalities that can be induced in normal human T cells infected in vitro with HIV. AIDS patients develop a variety of arthritic and dermatologic problems including an SS-like presentation (16-19) characterized by salivary gland lymphoid infiltrates with clinical enlargement, xerostomia, arthralgias and pulmonary lymphoid infiltrates (19). Infection with HIV must now be considered in any patient presenting with an SS-like clinical picture. However, they lack anti-Ro and anti-La autoantibodies. The absence of anti-Ro and anti-La autoantibodies favors retrovirus infection over autoimmune exocrinopathy in the differential diagnosis.

The increase in CD5+ B cells that occurs in SS (3), RA (4,5,20) and AIDS is another reason to suspect a retrovirus as the causative agent of SS. In mice, these cells are present in neonatal life after which they decline in normal strains but persist in autoimmune strains (6). In the latter, they become clonal late in life and infiltrate parenchymal lymphoid organs (21), resembling the pseudolymphoma stage of SS.

T cells of primary SS patients demonstrate abnormalities of transmembrane signalling after exposure of PMA and/or ionomycin (22). Similar abnormalities can be induced in normal human T cells infected in vitro with HIV (23). For these several reasons, evidence was sought for a retroviral infection in primary SS patients.

To search for a possible immune response to retroviral proteins in primary SS, immunoblotting was performed against HIV-1 proteins using serum from 47 patients with primary SS. A moderate to strong reactivity suggesting the presence of serum antibodies was found in 14 patients (30%). Of 100 normal subjects, only one was moderately positive. All 14 positive SS sera reacted against p24 (gag) but failed to react against gp41 or gp120 (env). Confirmation of specificity was obtained by reactivity with recombinant p24 and by blocking with recombinant p24. Two sera also reacted against p17. Four reacted against HIV-2 core proteins but none reacted with core proteins of HTLV-1. No serum reacted with equivalent molecular weight proteins from virus-free supernatants ("mock virus") or with uninfected cells from the cell line in which HIV-1 was propagated for use in the Western blot assay.

Only one of the 14 sera reacted against Ro and one other reacted against La. In primary SS, one would have expected 50% or more reactivity against Ro and La. These results identify a subset of SS patients characterized by 1) the presence of serum antibodies to HIV-1 group specific but not type specific proteins, and 2) the relative absence of anti-Ro and anti-La autoantibodies. In this latter respect, these SS patients constitute a subpopulation which resembles patients with HIV-induced SS-like disease.

The pattern of reactivity suggests that the immunogenic source is either an endogenous retrovirus or an exogenous virus different from any of the known retroviruses discovered to date.

IMMUNOASSAYS

Examples

The examples which follow are illustrative of laboratory techniques found by the present inventor to constitute preferred modes for practicing various aspects of the invention. However, those of skill in the art in light of the present disclosure will appreciate that various modifications and alterations can be made in the structuring and carrying out of the invention, and still remain within the spirit and scope of the invention.

The materials and methods listed below were employed in carrying out the studies reported in the particular enumerated examples which follow.

Serum From Sjogren's Syndrome (SS) and Systemic Lupus Erythematosus (SLE) Patients and Normal Donors.

SS and SLE patients were diagnosed according to established criteria (8, 33). Blood samples were obtained by venipuncture after informed consent. Serum was stored at −4° C. until studied for presence of antibodies to HIV-1 proteins by immunoblotting. Standard clinical laboratory studies were performed by routine procedures.

ELISA Assay

Antibodies to Ro and La were assayed using an enzyme-linked immunoassay (ELISA) employing purified antigens.

Western Blot Assays

An enzyme-linked immunoelectrotransfer blot (Western blot) technique was used to identify antibodies to HIV-related antigens. HIV-1 (strain HTLV-III) was propagated in cultures of the H9 subline of HUT 78 cells. HIV-1 partially purified, inactivated with psoralen and ultraviolet light and then detergent disrupted. Individual HIV proteins were resolved by electrophoresis on a sodium dodecyl sulfate-polyacrylamide slab gel before transfer to a nitrocellulose membrane. Strips of the nitrocellulose membrane were subsequently incubated with normal or SS serum. Immunoglobulins specifically bound to HIV proteins were visualized by a series of reactions using goat anti-human IgG conjugated with biotin, avidin conjugated horseradish peroxidase (HRP), and an HRP substrate (4-chloro-1-napthol).

The Western blot for HIV-1 was considered positive if bands were present at p24, p31 and either gp41 or gp160. In general, normal sera gave no reaction greater than 2-with any HIV-1 proteins (except for one normal subject who scored 2+ for p24). The reactions observed with SS sera were graded either −, +/−, 1+, 2+, 3+, 4+ or 5+ based on the intensity of reaction with p24.

A second source of p24 was a recombinant protein produced in the insect cell/baculovirus expression system (MicroGeneSys, Inc., West Haven, CT). This recombinant p24 is derived from an HIV-1 gag gene fragment that includes all of p24 plus 12 amino acids of the C-terminus of p17 and 57 amino acids of the N-terminus of p15.

Western blot assays were also used to determine the reactivity of serum antibodies to proteins of HIV-2 and HTLV-1. HIV-2 (strain LAV-2) propagated in HUT 78 cells and HTLV-I (strain) propagated in HUT 102 were partially purified and inactivated by the same procedures used for HIV-1.

As a control for reactions to cellular proteins present in virus preparations, Western blot assays were performed using nitrocellulose strips containing electrophoretically separated and transferred proteins from a "mock" virus preparation obtained by subjecting supernatants from uninfected H9 cells to the same purification and inactivation procedure used for virus preparation. Western blot assays were also performed using nitrocellulose strips containing electrophoretically separated and transferred proteins from whole cell lysates of uninfected H9 cells.

Example 1

Figure 1:
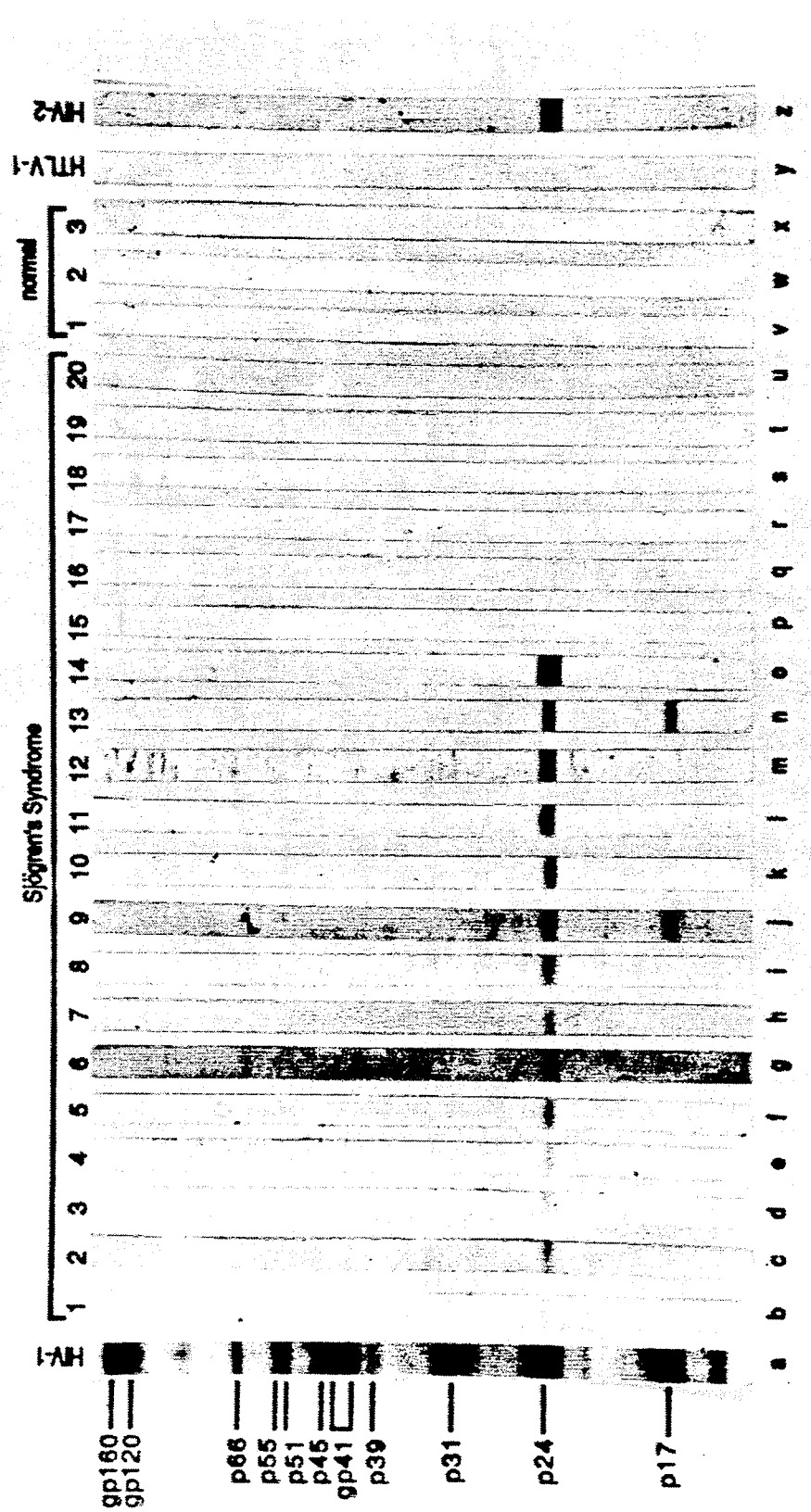
FIG. 1. Immunoblot Analysis of SS and Control Sera Reacting with HIV-1 Proteins

Identification of Antibodies Reacting With HIV-1 Proteins in Patients With SS and Normal Donors In the Western blot assay, sera from HIV-1 infected subjects may contain antibodies reactive to HIV proteins designated p17, p24, p31, gp41, p51, p55, p66, gp120, gp160 (the apparent $M_r$ of the proteins or glycoproteins in kilodaltons) (FIG. 1, lane a). Under the stringent conditions of this assay, reactivity against any protein present on the blots occurs in 1% of normal sera (1 in 100). In contrast to results with sera from normal control subjects, 14 of 47 sera (30%) from primary SS patients (FIG. 1) scored 2+ or greater reactivity against a protein with an $M_r$ identical to p24, the major core protein of HIV-1 (FIG. 1, lanes b-o). Significantly, two sera also reacted against a protein with an $M_r$ indistinguishable from p17, another of the HIV-1 gag proteins.

Example 2

Identification of Antibodies Reacting With HIV-2 and HTLV-1 Proteins in Patients With SS and Normal Donors To determine whether SS sera reacted generally to proteins present in preparations of human retroviruses, Western blot assays similar to the HIV-1 blots were used to determine reactivity to HIV-2 proteins (FIG. 2). Four SS sera reacted in the Western blot assay to p24 antigen derived from HIV-2 (strain LAV-2). Representative results are shown in FIG. 2, Panel A. The reactivities to the HIV-2 core protein were much reduced compared to the reactivities against HIV-1 proteins. These sera failed to display any reactivity against other virus-specific proteins present in the HIV-2 preparation; however, some of the sera were reactive against certain protein bands in the 50,000 to 70,000 $M_r$ range.

Although some individuals doubly infected with HIV-1 and HTLV-1 have been documented, antibodies from HIV-1 infected individuals which react against HIV-1 proteins generally fail to react with HTLV-1 proteins (including the major core protein). Likewise, antibodies from HTLV-1 infected subjects reactive with HTLV-1 proteins fail to react with HIV-1 proteins. By analogy and precedent established with infectious retroviruses in other species, these observations justify the separation of the HIVs and HTLVs into two distinct human retrovirus groups. Therefore, HTLV-1-containing virus preparations are an important control for our experimental findings. None of the 47 primary SS sera tested reacted against any HTLV-1-specific proteins (FIG. 2, Panel B).

Example 3

Identification of Antibodies Reacting With Recombinant p24 (p24*) in Patients With SS and Normal Donors The reaction against p24 and p17 could have been directed against cellular proteins not related to retroviral gag proteins. To rule this out, Western blot assays were performed using nitrocellulose strips containing electrophoretically separated and transferred proteins from a "mock virus" preparation. The latter was obtained by subjecting supernatants from uninfected H9 cells to the same inactivation and purification procedures used for virus preparation. SS sera, even those containing antibodies strongly reactive against p24 and p17 proteins present in HIV-1 preparations, failed to react with proteins of comparable $M_r$ in mock virus preparations.

To confirm reactivity against authentic retroviral gag protein, SS sera were incubated with various amounts of a recombinant gag protein produced in an insect cell/baculovirus expression system (MicroGeneSys). This protein, p24*, is produced from a gene fragment containing the entire p24 coding sequence and a portion of p17 and p12, and would be expected to bind to and block specific antibody interaction with HIV-1 p24. As a control we also incubated the p24* with sera from various HIV positive subjects. The recombinant p24 was capable of blocking the interaction of certain HIV-1 positive sera and most SS patient sera with HIV-1 p24 in Western immunoblots (FIG. 3, Panel A). As little a 1 ug p24* completely blocked the interaction of HIV-1 positive sera or SS sera with p24 from purified HIV-1 virions. Blocking appeared to be specific since the recombinant p24 failed to block the interaction of this HIV-1 positive sera with env proteins gp160 and gp120 or with gag-related proteins p17 and p66.

Figure 3B:
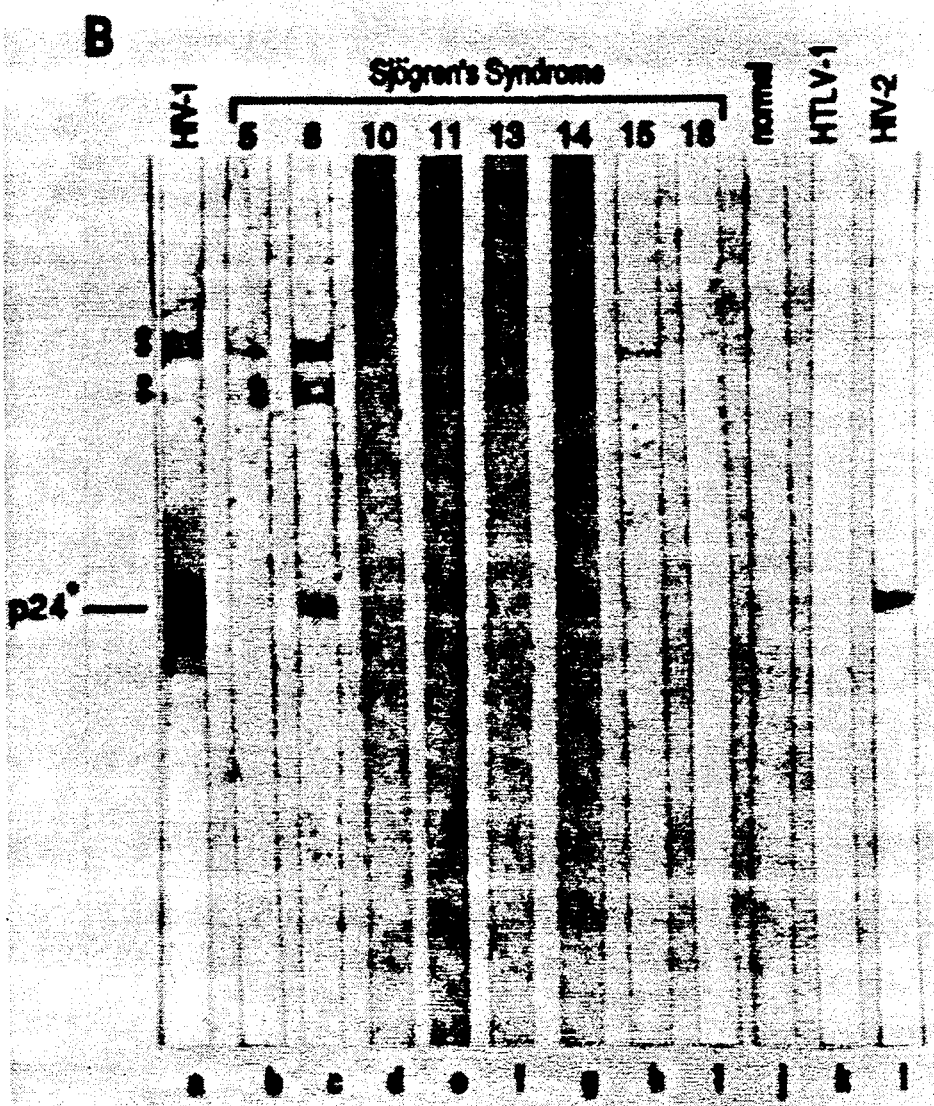

As further confirmation of specificity, p24* was separated by NaDodSo$_4$-PAGE and transferred to a nitrocellulose membrane. Strips of the nitrocellulose membrane were subsequently incubated with sera from SS patients or patients infected with other human retroviruses, and immunoglobulins specifically bound to the recombinant p24 were visualized by enzyme-linked immunoblotting. A serum from an HIV-1 positive patient with strong reactivity to p24 virions reacted strongly to the recombinant p24 (FIG. 3B, lane a) in the $M_r$ range of 70K (closed circles). Several SS sera with strong reactivity to p24 from HIV-1 virions also reacted with the recombinant p24 (FIG. 3B, lanes b-g). Most of the SS patient sera also recognized some proteins in the 70K range. Some of these may represent dimeric complexes of p24* since recombinant retroviral proteins from various sources tend to form detergent-stable multimeric complexes. An HIV-2 positive serum also reacted in the immunoblot assay to the recombinant p24 (lane 1). However, normal control serum (lane j) and an HTLV-1 positive serum failed to react with any protein on the strips containing p24*. These results with recombinant p24 confirm the specificity of the immunoblot assay. Reactivity of SS sera to recombinant p24 produced in bacteria (Cetus, Inc.) was also observed (data not shown).

Example 4

Clinical and Laboratory Correlations in Sjogren's Syndrome Patients Positive for Reactivity to p24

The 14 SS patients scoring 2+ or greater included 2 males and 12 females who ranged in age from 24 to 63 years. The focus scores on 9 labial salivary gland biopsies were all positive, varying from 2.5 to 12. One patient had a positive parotid biopsy. Importantly, these patients showed a wide spectrum of disease (Table 1). There were 4 patients with an SS/SLE overlap and 4 patients with neurologic disease (2 involving the central nervous system, 1 with Bell's palsy and 1 with peripheral neuropathy). One patient each had lymphoma, pseudolymphoma, polymyositis, chronic fatigue, recurrent episodes of "mononucleosis", and chronic renal failure.

These 14 patients cover virtually the entire clinical spectrum of SS, ranging from autoimmunity and SLE on the one hand to pseudolymphoma/lymphoma on the other. The patients as a group were remarkable for the paucity of Ro and La autoantibodies. Only one patient each had anti-Ro or anti-La (8%), whereas anti-Ro is positive in 45% of our total primary SS patients and even higher in some reported series (2). Thus, these fourteen patients stand out from other primary SS patients by having antibodies to p24 and lacking antibodies to Ro and La. In these two respects they are like HIV-1 positive patients who present with an SS-like clinical picture. They also resemble patients with HIV infection in presenting neurologically with dementia and hallucinations. However, they differ from HIV infected subjects in having with a chronic long-standing autoimmune disease (SS) which in some overlaps with SLE. Indeed, two of the patients in Table 1 have antibodies to Sm as well as to P24 (*, Table 1). Sm autoantibodies are generally considered a feature of SLE, occurring in approximately 35% of SLE patients and not in primary SS patients. An additional 5 patients with SLE, who lack SS, but have antibodies to p24 have been identified. Three of these patients also have anti-Sm autoantibodies.

Twenty-one patients with SLE who have moderate to strong reactivity against p24 gag of HIV-1 have been identified. Eighteen of these patients (86%) expressed an immunodominant Ig idiotype (Id 4B4) which is the product of a non-mutated germ line gene. This idiotype is evolutionary conserved (e.g., between mouse and man) and was originally detected with a human/human monoclonal antibody prepared from the peripheral blood of an SLE patient. In addition, 7 of the 21 SLE patients (33%) have anti-Sm binding activity, as does the monoclonal antibody described supra. Thus, the presence of antibodies to p24 gag and the absence of antibodies to env proteins of HIV-1 is positively correlated with the binding of an auto-antigen (Sm) and negatively correlated with the binding of two other autoantigens (Ro and La, Table 2). There is also a strong correlation between this anti-retroviral antigen profile and the presence of an immunodominant conserved idiotype (4B4), which is encoded by a $V_{HIII}$ germ line gene.

We have also identified 10 scleroderma patients who have antibodies to p24. Five of them have autoantibodies to topoisomerase I (Scl-7d, an antigen binding activity which is specific for schleroderma).

TABLE 1

| Sjogren's Syndrome Patients Positive For Reactivity to p24 | | | |
|---|---|---|---|
| Patient | p24 | Ro (SS-A) | La (SS-B) | Clinical Features |
| F.C. (1) | 2+ | − | + | SS/SLE |
| M.C. (2) | 2+ | − | − | Peripheral Neuropathy |
| S.E. (3) | 2+ | − | − | CNS |
| G.F. (4) | 2+ | − | − | CNS |
| B.P. (5) | 2+ | − | − | SS/SLE* |
| B.R. (6) | 2+ | − | − | Chronic Renal Failure (? cause) |
| M.Y. (7) | 2+ | + | − | SS/SLE |
| K.B. (8) | 3+ | − | − | Lymphoma |
| M.B. (9) | 3+ | − | − | Bell's Palsy |
| J.S. (10) | 3+ | − | − | Psudolymphoma |
| A.C. (11) | 4+ | − | − | Polymysitis |
| B.F. (12) | 4+ | − | − | Recurrent Episodes of "monoucleosis" |
| D.T. (13) | 4+ | − | − | Chronic Fatigue |
| N.C. (14) | 5+ | − | − | SS/SLE* |

*Antibodies to Sm present

TABLE 2

Correlations Between Antibodies to Retroviral Antigens, Autoantigens, Idiotypes and Unmutated $V_H$ Genes

| Disease | No. of Patients With p24 Antibodies | Autoantigen Positive | Negative | Idiotype | $V_H$ Gene |
|---|---|---|---|---|---|
| SS | 14 | | Ro La | | |
| SLE | 21 | Sm(snRNP) | | 4B4 | $V_H$III germline |
| S | 10 | Scl-7d topoisomerase-I | | | |

SS = Sjogren's Syndrome
SLE = Systemic Lupus Erythematosus
S = Scleroderma

Example 5

Identification of Antibodies Reacting With HIV-1 Proteins in Patients With Systemic Lupus Erythematosus (SLE) and Normal Donors In the Western blot assay, sera from HIV-1 infected subjects may contain antibodies reactive to HIV proteins designated p17, p24, p31, gp 41, p51, p55, p66, gp120, gp160 (the apparent $M_r$ of the proteins or glycoproteins in kilodaltons). Under the stringent conditions of this assay, reactivity against any protein present on the blots occurs in 1% of normal sera (1 in 100). In contrast to results with sera from normal control subjects, 21 of 60 sera (35%) from SLE patients scored 2+ or greater reactivity against a protein with an $M_r$ identical to p24, the major core protein of HIV-1. Some two sera also reacted against a protein with an $M_r$ indistinguishable from p17, another of the HIV-1 gag proteins.

SS is related closely to systemic lupus erythematosus (SLE). Indeed, four of the 14 SS patients with serum antibodies to p24 (Example 1) also had SLE. Interestingly, these four were the only patients among the 14 who expressed the 4B4 idiotype (Table 2; associated with Sm binding and utilization of a $VH_{III}$ germ line gene). Two of these four SS/SLE overlap patients also had autoantibodies to the Sm nucleoprotein, an autoantibody activity present in 30% of SLE patients and absent in primary SS. Sm is a small nuclear ribonucleoprotein involved in splicing (13). Thus, a total of 21 SLE patients are positive for anti-p24 protein.

Example 6

SLE Patients Positive For Antibodies To Retroviral GAG Protein p24 Correlated With Presence Of 4B4 Idiotype Eighteen out of the 21 anti-p24 positive SLE patients express the 4B4 idiotype (Table 3) which have previously shown to be the product of a non-mutated germ line gene (3). Seven of these patients bind SM (*), consistent with previous observation of an incomplete relationship between Id 4B4 and antibodies to Sm. Competitive inhibition studies in these five patients demonstrated that Sm could block the binding of p24 about 33%, suggesting the presence of epitopes shared between the retroviral gag protein p24 and the an RNP Sm. These results suggest that Sm may be the internal image for p24 gag, and that "autoantibodies" to nuclear components that occur frequently in SLE may arise by immunization to viral components and therefore do not represent anti-self reactions.

TABLE 3

Systemic Lupus Erythematosus Patients
Positive For Antibodies to Retroviral Gag Protein p24

| Patient | p24 (21/21) | ID 4B4 (18/21) | Sm Antibody (7/21) |
|---|---|---|---|
| Th.T | 2+ | − | − |
| J.K. | 2+ | + | + |
| A.C. | 2+ | + | + |
| I.T. | 2+ | + | − |
| C.C. | 2+ | + | − |
| F.C. | 2+ | + | − |
| B.P. | 2+ | + | + |
| M.Y. | 2+ | + | − |
| B.A. | 2+ | + | + |
| S.P. | 2+ | − | + |
| R.M. | 2+ | − | − |
| M.S. | 2+ | + | − |
| G.T. | 2+ | + | − |
| M.Z. | 2+ | + | − |
| J.E. | 2+ | + | − |
| C.O. | 2+ | + | − |
| I.V. | 3+ | + | − |
| F.G. | 3+ | + | − |
| G.W. | 4+ | + | + |
| N.C. | 5+ | + | + |
| S.C | 5+ | + | − |

Example 7

Identification of Antibodies Reacting With HIV-1 Proteins in Patients With Other Autoimmune Rheumatic Diseases In the Western blot assay, sera from HIV-1 infected subjects may contain antibodies reactive to HIV proteins designated p17, p24, p31, gp41, p51, p55, p66, gp120, gp160 (the apparent $M_r$ of the proteins or glycoproteins in kilodaltons) (FIG. 4, lane a). Under the stringent conditions of this assay, reactivity against any protein present on the blots occurs in 1% of normal sera (1 in 100). In contrast to results with sera from normal control subjects, 10 of 20 sera (50%) from Scleroderma patients (FIG. 4, PSS or CREST or CREST/SS) scored 2+ or greater reactivity against a protein with an $M_r$ identical to p24, the major core protein of HIV-1 (FIG. 4, lanes b-u).

Thus, ten patients with scleroderma and 4 patients with rheumatoid arthritis have anti-p24 antibodies. Therefore, 14 patients with SS, 21 patients with SLE, 10 patients with scleroderma and 4 patients with rheumatoid arthritis have anti-p24 gag HIV-1 antibodies. These patients are reacting immunologically to HIV-1 retroviral proteins but they are not infected with HIV-1, HIV-2 or HTLV-1.

Discussion

Autoimmune diseases are said to be multifactorial with genetic, immunologic, virologic and hormonal factors all playing a role. The etiology of autoimmune disease is poorly understood. No chronic autoimmune disease of humans is known to be caused by a virus. However, the findings represented by the present invention reveal the possibility of retroviral infection as the cause of autoimmune exocrinopathy (primary SS).

Thirty percent of sera obtained from patients with primary SS contained antibodies that reacted in immunoblot with p24, an HIV-1 gag protein. Certain sera (2/14) also reacted with p17. None reacted with the envelope protein gp120. Four sera also reacted against HIV-2 core proteins but not against core proteins of HTLV-1 or against extracts prepared from supernatants or cells of the line in which the virus was grown. Sera reacting with p24 of HIV-1 also reacted with recombinant p24. The latter can block the reaction of SS sera with p24. Although false positive reactions to p24 have been reported (24,25), and remains a remote possibility in the investigations which form the basis of the invention, the foregoing results do suggest a possible retroviral etiology for SS.

Because the immunoblot assay is arguably subject to observer bias, any serum specimen scoring less than 2+ was not graded as positive. The significance of a 1+ (seen in 13 SS patients but also in normal subjects) is unknown. The presence of these reactions in presumably normal (but also occupationally exposed) individuals remains to be determined. The true incidence of antibodies to p24 in primary SS must await further analysis of patients and more normal subjects showing a+ reactivity. Thus, the 30% incidence reported here should be considered a minimal estimate.

SS patients demonstrating an immune response to p24 represent almost the entire clinical spectrum of this illness, yet have in common a paucity of autoantibodies to Ro and La. Of the 14 patients, only one had antibodies to Ro and another had antibodies to LA. By contrast, anti-Ro antibodies are present in 45% of the total SS clinic population studies above. Even higher percentages have been reported in the literature (8).

This lack of anti-Ro and anti-La is strikingly reminiscent of what is seen in patients infected with HIV-1 and presenting with parotid gland swelling, xerostomia or other features of SS including rheumatoid and antinuclear factor positivity (24). The 14 patients identified by the assay were clearly not infected with the classical HIV-1 or HIV-2 agents as determined by their profile on Western blots. One might conclude, therefore, that when a retrovirus (be it HIV-1 or the presumed virus suggested by the above described findings) causes an SS-like disease, autoantibodies to Ro and La are not to be expected.

The 14 "positive" patients, all living, included four patients with overlap features of both SS and SLE, another four with neurologic involvement (peripheral in two and central in two) and one patient each with chronic fatigue, recurrent "mononucleosis", chronic renal failure, lymphoma, pseudolymphoma and polymyositis. Two patients with CNS disease had features of dementia with hallucinations in one and failing memory in the other. Polymyositis is an idiopathic condition that has been reported in AIDS (25).

As a group, these 14 patients would not stand out clinically from the other 35 patients investigated in these studies found in the general experience. Thus, a subset of primary SS patients are identified by the assay who are not distinguishable clinically but only by the presence of antibodies to a retroviral gag protein. It is, thus, recommended that screening for anti-p24 be performed in every SS patient, particularly if anti-Ro and/or anti-La is absent. SS patients with anti-p24 are potential candidates for anti-viral therapy, such as AZT.

The pattern of Western blot reactivity observed in the 14 retroviral "positive" SS patients, i.e., reactivity against p24 gag and in some cases p17 gag of HIV-1, reactivity of some sera with p24 of HIV-2, and the failure to react with HTLV-1 core proteins, in consistent with exposure to a virus of the HIV group of human retroviruses. The lack of immunologic reaction in these patients to type-specific determinants of either HIV-1 or HIV-2 which are generally present on envelope proteins, suggests that these patients are reacting either against an agent distinct from any of the known human retroviruses, or against endogenous human retroviruses which may have antigenic similarities to HIV gag proteins p24 and p17.

Although endogenous retrovirus sequences are not generally expressed, this question has not been explored in tissues from patients with autoimmune disorders. It is interesting that some manifestations of illness in our patients (dementia, chronic fatigue, CNS involvement, purpura neuro polymyositis) recall the symptom complex of HIV infection. However, in lieu of immunodeficiency we have immunologic exuberance (autoimmunity). How such a virus might induce features of SLE is an intriguing biologic question whose answer could well lead to important new insights regarding the association between retroviral infection and autoimmunity.

Antibodies reactive to HTLV-1 proteins occur in SLE sera. However, the results in SLE were obtained by ELISA and may represent reactivity to cellular proteins present in retroviral preparations. As reported here, SS sera do not contain antibodies reactive against HTLV-1 proteins.

Although there is no precedent for associating a human retrovirus with a rheumatic disease, there is evidence associating HIV-1, HTLV-1 and HTLV-II with neurologic disorders. Antibodies reacting with the HTLV-1 gag protein have been found in serum and cerebrospinal fluid (CSF) from patients with multiple sclerosis (MS, 26). In one-third of patients, in situ hybridization revealed sequences of HTLV-1 in lymphocytes cultured from the CSF. More recently, such sequences were found in peripheral blood mononuclear cells from six of six MS patients but in only one of 20 control subjects using techniques of gene amplification and molecular cloning (27).

MS has some features of an autoimmune disease as does infection with HIV virus (28). Moreover, an MS-like disease has been reported in patients with primary SS (29). The presence of oligoclonal immunoglobulin bands in the CSF is common in MS, just as monoclonal and oligoclonal immunoglobulins occur frequently in primary SS (9-15) and also in HIV positive individuals where they have been identified as HIV-specific (30).

Pulmonary lymphoid infiltration is a common feature of extraglandular SS and is included in the definition of pseudolymphoma (10). Pulmonary lymphoid infiltrates were found as part of a systemic disease including lymphadenopathy and splenomegaly in transgenic mice containing HIV proviral DNA (31). Similar pulmonary interstitial infiltrates are also seen in adult AIDS patients in naturally occurring lentivirus infections.

SS may be accompanied by a second autoimmune rheumatic disease, most often rheumatoid arthritis. Such patients are said to have secondary SS. If a viral etiology can be demonstrated for primary SS, it may be true for secondary SS as well and by extrapolation for other autoimmune rheumatic diseases without SS.

Definitive proof or an association between primary SS and retrovirus infection must await isolation of the virus from the tissues of SS patients. An ability to demonstrate antibodies to p24 of HIV-1 or HIV-2 in one-third of primary SS patients might mean that additional viruses may also be involved in the etiology of SS. Perhaps not all SS patients develop a humoral immune response to each of the gag determinants conserved among members of the HIV group. A retrovirus has already been implicated in the pathogenesis of chronic arthritis in goats (32). If such a virus can be isolated from tissue of autoimmune disease patients, it is proposed that it be called Human Autoimmunity Virus in keeping with the currently accepted nomenclature for the AIDS virus.

The present invention has been disclosed in terms of preferred modes found to work well in the practice of the invention. However, numerous modifications and changes in the steps, procedures used and materials will become apparent to those of skill in the art in light of the disclosure. For example, changes in the manner in which the respective retroviral antigens are identified will become apparent. Moreover, there is no requirement that the same analytical approach (i.e., antibody antigen or nucleic acid) be used for determination of the presence of group-specific antigens and absence of HIV1 type-specific antigen. Similar, modifications and improvements in the techniques used for identifying patients will be apparent in light of the disclosure. These and other modifications are intended to be within the spirit of the present invention and scope of the appended claims.

References

The references listed below are incorporated herein by reference to the extent that they supplement, explain, provide a background for or teach methodology, techniques and/or compositions employed herein.

1. Provost et al. (1988), *J. Inv. Derm.*, 91:369-371.
2. Talal et al. (1985) *Proceedings of the International Congress of Rheumatology*, ILAR '85, Sydney, Australia.
3. Dauphinee et al. (1988), *Arth. Rheum.*, 31:642-647.
4. Dauphinee et al. (1986), *Sixth Int'l Cong. Immunol.*, Toronto, Canada.
5. Hardy et al. (1987), *Science*, 236:81-83.
6. Hayakawa et al. (1984), *Proc. Natl. Acad. Sci. USA*, 2494-2498.
7. Strand et al. (1980), *Bull. Rheum. Dis.*, 30:1046-1052.
8. Talal et al. (1987), Sjogren's Syndrome Clinical and Immunological Aspects. Springer-Verlag, Heidelberg.
9 Talal et al. (1964), *Am. J. Med.*, 3:529-540.
10. Talal et al. (1967), *Am. J. Med.*, 43:50-65.
11. Moutsopoulos et al. (1985), *Ann. Rheum. Dis.*, 44:109-112.
12. Tzioufas et al. (1986), *Arthritis Rheum.*, 29:1098-1104.
13. Talal, N. (1988), *J. Autoimmunity*, 1:171-184.
14. Zulman et al. (1978), *N. Enol. Med.*, 299:1215-1220.
b 15. Provost et al. (1988), *J. Inv. Derm.*, 91(4):369-371.
16. Coudere et al. (1987), *Arch. Intern. Med.*, 147:898-901.
17. de Clerk et al. (1988), *Arthritis Rheum.*, 31:272-275.
18. Ulirsch et al. (1987), Human Pathol., 18(10):1063-1068.
19. Schoidt et al. (1989), *J. Autoimmunity*. (in press).
20. Plater-Zyberk et al. (1985), *Arthritis Rheum.*, 28:971-976.
21. Stall et al. (1988), *Proc. Natl. Acad. Sci. USA*, 85:7312-7316.
22. Dauphinee et al. (1989), *Arthritis Rheum.*, (in press).
23. Linette et al. (1988), *Science*, 241:573-576.
24. Talal, N. (1988), *J. Autoimmunity*, 1:703-709.

25. Darakas et al. (1986), *JAMA*, 256:2381-2383.
26. Koprowski et al. (1985), *Nature*, 154:160.
27. Reddy et al. (1989), *Science*, 243:529-534.
28. Kopelman et al. (1988), *Amer. J. Med.*, 84:82-88.
29. Alexander et al. (1986), *Annals Int. Med.*, 104:323-330.
30. Papadopoulos et al. (1988), *Clin. Chem.*, 34(5):973-975.
31. Leonard et al. (1988), *Science.* 242:1665-1670.
32. Crawford et al. (1980), *Science,* 207:997-999.
33. Dang et al. (1988), *Clin. Exp. Immunol.,* 71:445-450.

What is claimed is:

1. A method for identifying a human individual having an increased probability of having Sjorgren's syndrome (SS), which individual does not have AIDS and is not infected with a human immunodeficiency virus, the method comprising the steps of:
    (a) obtaining a sample from such an individual that includes antibodies;
    (b) determining if said sample is (i) free of antibodies to HIV-type specific antigens selected from the group consisting of gp41, gp120 and gp160, and (ii) lacks anti-Ro and anti-La antibodies;
    (c) determining the presence in said sample of antibodies to one or more group-specific retroviral antigens selected from the group consisting of p24 and p17 gag proteins; and
    (d) correlating the absence of anti-Ro and anti-La autoantibodies, the absence of HIV-type specific antibodies and the presence of antibodies to said group-specific antigens with an increased probability of said individual having SS.

2. The method of claim 1, wherein the sample of step (a) comprises serum.

3. The method of claim 1, wherein step (c) the group specific retroviral antigen is p24 gag protein.

4. The method of claim 1, wherein step (c) the group specific retroviral antigen is 17 gag protein.

5. The method of claim 1, wherein step (b)(i) the HIV-type specific antigen is gp41.

6. The method of claim 1, wherein step (b)(i) the HIV-type specific antigen is gp120.

7. The method of claim 1, wherein step (b)(i) the HIV-type specific antigen is gp160.

8. The method of claim 1, wherein step (b)(i) the HIV-type specific antigen is an anti-Ro autoantibody.

9. The method of claim 1, wherein step (b)(ii) the HIV-type specific antigen is an anti-La autoantibody.

10. The method of claim 1 wherein determining the antibodies of step (b) or step (c) comprises performing a Western blot, ELISA or RIA on the sample to determine the presence or absence of the respective retroviral antigens.

* * * * *

UNITED STATES PATENT AND TRADEMARK OFFICE
CERTIFICATE OF CORRECTION

PATENT NO.   :   5,320,940

DATED        :   June 14, 1994

INVENTOR(S)  :   Talal et al.

It is certified that error appears in the above-identified patent and that said Letters Patent is hereby corrected as shown below:

In claim 8, column 20, line 20, change "(i) to --(ii)--.

Signed and Sealed this

Sixth Day of September, 1994

Attest:

BRUCE LEHMAN

Attesting Officer        Commissioner of Patents and Trademarks